United States Patent
Wang et al.

[11] Patent Number: 6,073,038
[45] Date of Patent: *Jun. 6, 2000

[54] EXTENDED LIFE DISPOSABLE PULSE OXIMETRY SENSOR

[75] Inventors: Huisun Wang, Hamden; David R. Rich, Glastonbury; Barry J. Feldman, Cheshire, all of Conn.

[73] Assignee: NTC Technologies, Inc., Wilmington, Del.

[ * ] Notice: This patent is subject to a terminal disclaimer.

[21] Appl. No.: 09/178,131

[22] Filed: Oct. 23, 1998

Related U.S. Application Data

[63] Continuation of application No. 08/592,919, Jan. 29, 1996, Pat. No. 5,891,026.

[51] Int. Cl.[7] ........................................................ A61B 5/00
[52] U.S. Cl. ........................ 600/323; 600/310; 600/344; 600/479
[58] Field of Search ..................................... 600/309–310, 600/322–324, 344, 473, 476–479

[56] References Cited

U.S. PATENT DOCUMENTS

| | | |
|---|---|---|
| Re. 36,000 | 12/1998 | Swedlow et al. . |
| 4,685,464 | 8/1987 | Goldberger et al. . |
| 4,825,879 | 5/1989 | Tan et al. . |
| 4,830,014 | 5/1989 | Goodman et al. . |
| 4,865,038 | 9/1989 | Rich et al. . |
| 4,928,691 | 5/1990 | Nicolson et al. . |
| 5,109,849 | 5/1992 | Goodman et al. . |
| 5,170,786 | 12/1992 | Thomas et al. . |
| 5,209,230 | 5/1993 | Swedlow et al. . |
| 5,217,012 | 6/1993 | Young et al. . |
| 5,337,744 | 8/1994 | Branigan . |
| 5,438,986 | 8/1995 | Disch et al. . |
| 5,469,845 | 11/1995 | DeLonzor et al. . |

*Primary Examiner*—Cary O'Connor
*Assistant Examiner*—Ryan Carter
*Attorney, Agent, or Firm*—Trask, Britt & Rossa

[57] ABSTRACT

An oximetry sensor comprising a foam wrap member including a fastener, back film mounting member, LED assembly and photodiode connected to a cable, support rings for the LED assembly and photodiode, window film for the LED assembly and photodiode, and a top liner.

23 Claims, 5 Drawing Sheets

EXTENDED LIFE DISPOSABLE PULSE OXIMETRY SENSOR

CROSS REFERENCE TO RELATED APPLICATION

This application is a continuation of application Ser. No. 08/592,919, filed Jan. 29, 1996, now U.S. Pat. No. 5,891,026.

BACKGROUND OF THE INVENTION

1. Field of the Invention

The present invention is related to sensors applied to the body for monitoring or making measurements of body tissue conditions, metabolism or other body functions indicative of health. More specifically, the present invention is directed to a pulse oximetry sensor which can be readily attached and reattached to a portion of the body in a non-invasive manner.

2. State of the Art

In the prior art, a non-invasive pulse oximetry sensor may be used to measure the relative oxygen saturation of the blood. Typically, in such prior art types of oximetry sensors a light source, such as a light emitting diode (LED) is used to alternately direct light of two different wave lengths, such as red and infra-red light, to the blood through the skin. The light transmitted or reflected by the blood at the different wave lengths can be then compared to provide a measurement of oxygen saturation of the blood.

A typical prior art probe system contains the light emitting sources, such as the LED's, and a light sensor, such as a photo diode, mounted on the appendage of the body, such as a finger, toe, ear lobe, nose, hand, tongue or foot. However, such devices need to be capable of being readily attached to the body appendages, comfortable when attached to a patient, reusable on the same patient, and relatively inexpensive to manufacture.

One type of prior art type oximetry sensor uses the mechanical clamping action of spring biased jaws to retain the sensor on an appendage of a patient. Such a device is illustrated in U.S. Pat. Nos. 4,685,464 and 5,438,986. While such devices are effective, they are inherently difficult to clean and inappropriate for the long term use or application on a patient.

Another type of oximetry sensor relies upon a deformable member being located in the device to retain the sensor on the appendage of a patient. Such a device is illustrated in U.S. Pat. Nos. 4,865,038, 4,928,691, and 5,217,012. During the reuse of such sensors on a patient since the retaining member has been deformed and has a memory, reinstallation of the sensor may affect the comfort of the patient. Also, such sensors are also relatively expensive to manufacture as the sensors contain a number of components.

In yet another type of oximetry sensor in an effort to facilitate reuse of the sensor and to provide comfort to the patient during use of the sensor, the sensor is retained on the finger of a patient through the use of hook and loop fabric. However, such sensors have used complex shapes of hook and loop fabric as retaining devices thereby causing the manufacturing expense of the device to increase. Such sensors are illustrated in U.S. Pat. Nos. 4,825,879, 5,209,230, and 5,469,845.

In another type of oximetry sensor, adhesive is used to attach the sensor to a patient in an attempt to lower manufacturing cost of the sensor, provide comfort to the patient during use of the sensor, and provide a secure attachment of the sensor to the patient. However, since the device must be frequently repositioned on a patient, the adhesive loses its adhesive quality during reuse. Also, the adhesive may irritate the patient during use thereby causing discomfort. Such sensors are illustrated in U.S. Pat. Nos. 4,830,014 and 5,170,786.

In yet another type of oximetry sensor, an elastomeric member is used to retain the sensor on the finger of a patient. Although this allows reuse of the sensor, the degree of pressure applied by the elastomeric member and the elastomeric member being in contact with the skin may cause discomfort to a patient. Such a sensor is illustrated in U.S. Pat. No. 5,337,744.

Since the prior art sensors are generally either reusable and expensive to manufacture, or are not easily reusable and have a relatively low manufacturing cost, or reusable and cause discomfort to the patient, there is a need for a comfortable, extended life, disposable, low manufacturing cost pulse oximetry sensor.

SUMMARY OF THE INVENTION

The present invention is directed to a comfortable, extended life, disposable, low manufacturing cost pulse oximetry sensor. The present invention is also directed to the method of making such an oximetry sensor. The oximetry sensor of the present invention comprises a foam wrap member including a fastener, back film mounting member, LED assembly and photodiode connected to a cable, support rings for the LED assembly and photodiode, window film for the LED assembly and photodiode, and a top liner.

The oximetry sensor and the method of manufacture of the present invention will be better understood when the drawings are taken in conjunction with the description of the invention.

DESCRIPTION OF THE INVENTION

Figure 1:
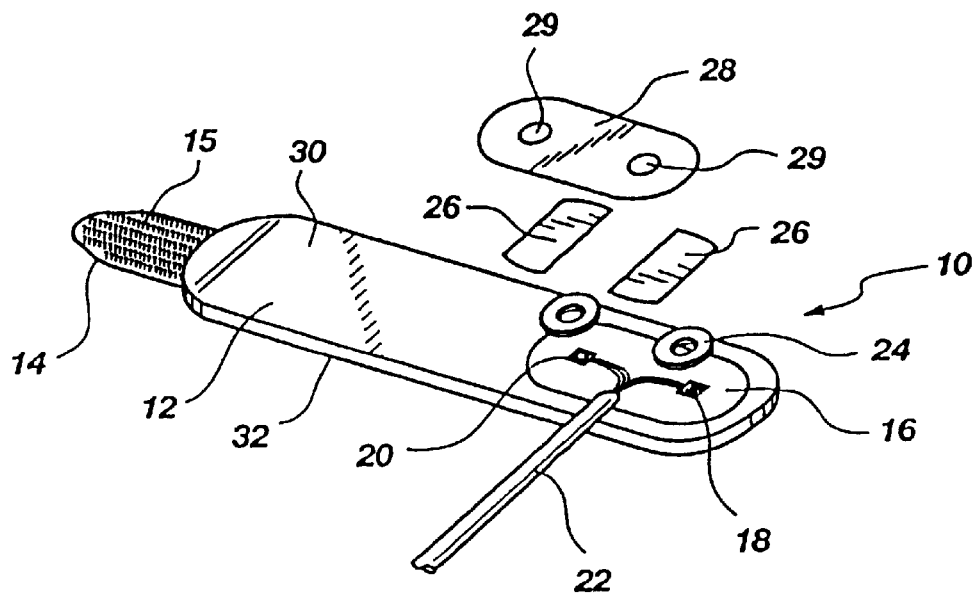
FIG. 1 is an exploded view of the oximetry sensor of the present invention.

Referring to drawing FIG. 1, the oximetry sensor 10 of the present invention is shown in an exposed view. The oximetry sensor of the present invention comprises a foam wrap member 12 including a fastener 14, back film mounting member 16, LED assembly 18 and photodiode 20 connected to a cable 22, support rings 24 for the LED assembly 18 and photodiode 20, window film 26 for the LED assembly 18 and photodiode 20, and a top liner 28.

The foam wrap member 12 comprises a fabric and foam lamination having a fastener attached thereto. The foam portion 30 of the foam wrap member 12 comprises any suitable type foam, such as a polyester foam. The fabric portion 32 of foam wrap member 12 comprises any suitable fabric, such as a fabric having a plurality of loops integrally formed therein, which may be readily engaged by a plurality of fastening members located on the fastener 14 of the foam wrap member 12. The fastener 14 attached to the foam wrap member 12 comprises a molded plastic member having a plurality of hooks 15 formed on one surface thereof to engage the plurality of loops formed in the fabric portion 32 of the foam wrap member 12. The combination of the fastener 14 having a plurality of hooks 15 formed on one surface thereof and the fabric portion 32 of the foam wrap member 12 is commonly referred to as a VELCRO type fastener comprised of synthetic materials which adhere when pressed together. The foam portion 30 and fabric portion 32 of the foam wrap member 12 are secured together by any suitable means of fastening, such as adhesive bonding. The fastener 14 of the foam wrap member 12 is secured to the foam portion 30 and fabric portion 32 of the foam wrap member 12 by any suitable means, such as adhesive bonding, sewing, ultrasonic staking, the natural tendencies of these materials to adhere to each other, etc.

The back film mounting member 16 comprises any suitable plastic film member, such as polyethylene film, having any suitable adhesive coating on each side thereon to adhesively retain the back film mounting member 16 to the foam portion 30 of the foam wrap member 12 and adhesively attach the LED assembly 18 and photodiode 20 thereto. While the back film mounting member 16 serves to adhesively attach the LED assembly 18 and photodiode 20 to the foam wrap member 12, the back film mounting member may be deleted and the assembly 18 and photodiode 20 adhesively retained on the foam wrap member 12 by other means, such as by the top liner 28.

The LED assembly 18 includes a red light emitting diode and an infrared light emitting diode adjacently mounted forming a rectangular shaped member. As is known in oximetry, the transmission of light in the red range of the spectrum, i.e., at a wave length of approximately 660 nanometers through blood is substantially affected by the amount of oxygenated hemoglobin present in the blood. The transmission of light in the infra-red range of the spectrum, i.e., at a wave length of approximately 940 nanometers through blood is substantially unaffected by the amount of oxygenated hemoglobin present in the blood. Oximeters use this principle to alternately illuminate the blood through the tissue with light of the foregoing respective wave lengths.

The photodiode 20 is sensitive to red light and infrared light. The photodiode 20 alternately senses radiated red and infrared energy.

The cable 22 is connected to the LED assembly 18 and photodiode 20 via suitable wire connections thereto. The cable 22 includes a suitable connector 40 (not shown) on the end thereof for connecting the LED assembly 18 and photodiode 20 to a suitable display. Alternatively, the LED assembly 18 and photodiode 20 may be connected to a suitable device through the use of a flexible printed circuit or the like.

The support rings 24 are formed of any plastic material suitable for use with the LED assembly 18 and photodiode 20, such as a soft pliant rubber like material. The support rings 24 are installed around the LED assembly 18 and photodiode 20 to provide comfort to the patient during use of the pulse oximetry sensor. Alternately, if the foam wrap member 12 is of sufficient thickness for comfort to the patient or a thin LED assembly 18 and photodiode 20 are used, the support rings 24 may be eliminated.

The window film 26 is used to cover the support rings 24 surrounding the LED assembly 18 and photodiode 20. The window film 26 should be transparent to red and infra-red light and allow the transmission thereof therethrough readily. The window film 26 may be of such material as polyethylene or the like. The window film 26 is adhesively coated on one side thereof to retain the support rings 24, LED assembly 18, and photodiode 20 and be secured to the back film mounting member 16.

The top liner 28 comprises a highly comfortable and breathable polyurethane material having two polyethylene windows 29 therein for the transmission of red and infra-red light therethrough. If desired, the top liner 28 may be coated with a suitable adhesive coating on one side thereof to adhesively bond to the window film 26 and to the back film mounting member 16. However, it is not necessary that the top liner 28 be coated with adhesive on one side thereof as the back film mounting member 16 is coated with adhesive to adhesively bond the LED assembly 18, photodiode 20, support rings 24, window film 26, and the top liner 28 thereto.

Figure 2:
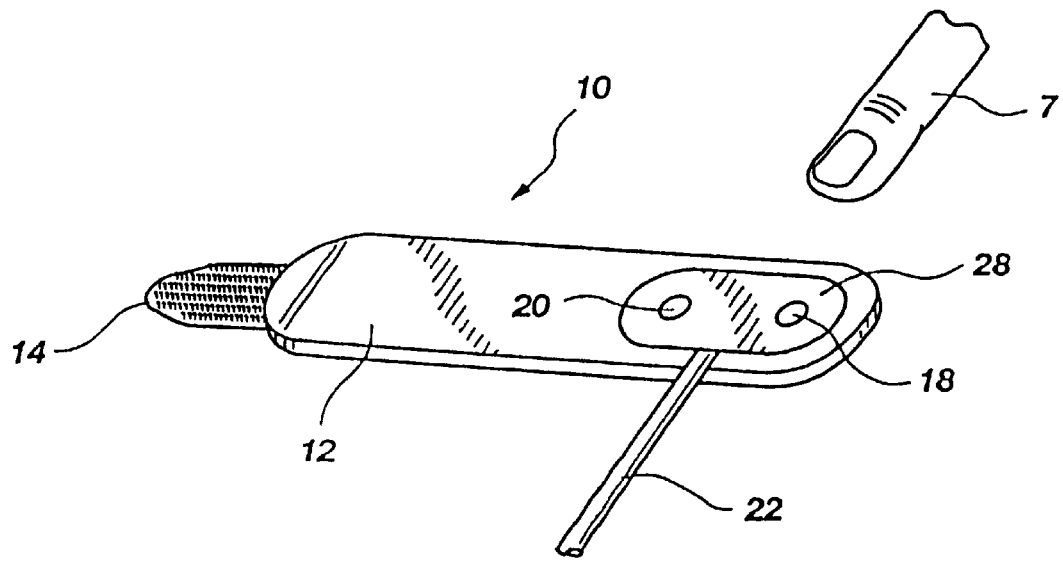
FIG. 2 is a view of the oximetry sensor of the present invention in relation to the finger of a patient before the oximetry sensor is installed thereon.

Referring to drawing FIG. 2, the oximetry sensor 10 of the present invention is shown in relation to the finger 7 of a patient before the installation thereon. As shown, the oximetry sensor 10 comprises a generally elongated rectangular shaped foam wrap member 12 which is initially disposed generally perpendicularly to the finger 7 of a patient before the installation thereon. The LED assembly 18 and photodiode 20 are generally arranged to be located on opposite sides of the patient's finger 7 when the pulse oximetry sensor is installed thereon. The pulse oximetry sensor 10 of the present invention may be used on other sites of a patient, such as the heel, etc., depending upon the desired point of application.

Figure 3:
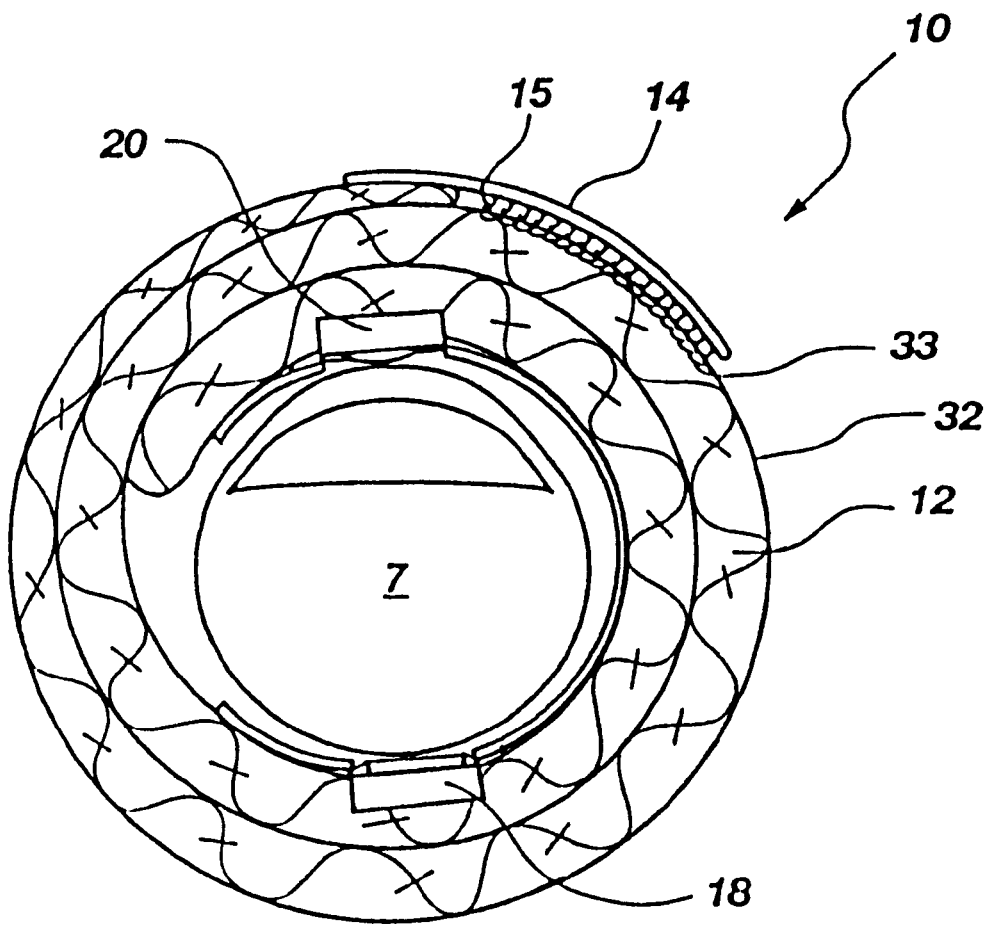
FIG. 3 is a view of the oximetry sensor of the present invention installed on the finger of a patient.

Referring to drawing FIG. 3, the oximetry sensor 10 is shown installed on the finger 7 of a patient. As installed, the oximetry sensor 10 is wrapped around the finger 7 of a patient so that the LED assembly 18 is located generally opposite the photodiode 20 in engagement with the skin and/or the fingernail of the finger 7. In this manner, the red and infra-red light emitted from the LED assembly 18 is transmitted through the tissue of the finger 7 and detected by the photodiode 20. The foam wrap member 12 of the oximetry sensor 10 is generally wound around the finger 7 so that the fastener 14 having hooks 15 thereon of the member 12 releasably engages the loops 33 of the fabric portion 32 of the member 12. To adjust the oximetry sensor 10 on the finger 7 of a patient since the foam wrap member 12 is compressible and conformable, the member 12 may be rotated around the finger 7 without unfastening or the fastener 14 being disengaged or removed from engaging the fabric portion 32 of the foam wrap member 12 and the member 12 unwrapped from engaging the finger 7. Since the foam wrap member 12 is compressible and conformable, the amount of force caused by the wrapping of the oximetry sensor 10 around the finger 7 may be adjusted and controlled to provide the desired amount of force during use without causing discomfort or trauma to the finger 7 of a patient. Additionally, since the fastener 14 may be engaged with the fabric portion 32 of the foam wrap member 12 for repeated installation, adjustment, and removal of the sensor 10 from the finger 7 of a patient, the oximetry sensor 10 can be repeatedly reused on the same patient without any substantial loss of fastening ability.

Figure 4:
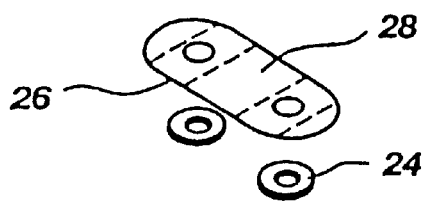
FIG. 4 is a view of the first step of the method of manufacture of the oximetry sensor of the present invention.

Referring to drawing FIG. 4, the first step in the manufacture of the oximetry sensor 10 is illustrated. The top liner 28 is formed having the window film 26 adhesively bonded thereto with the window film 26 having an adhesive coating on the bottom side also; i.e., the window film 26 is adhesively coated on one side. Next, the support rings 24 are placed on the bottom of the window film 26 being retained thereon by the adhesive on the bottom of the window film 26. As previously stated, the use of the support rings 24 is optional depending upon the amount of cushioning provided by the foam wrap member 12 for the comfort of the patient.

Figure 5:
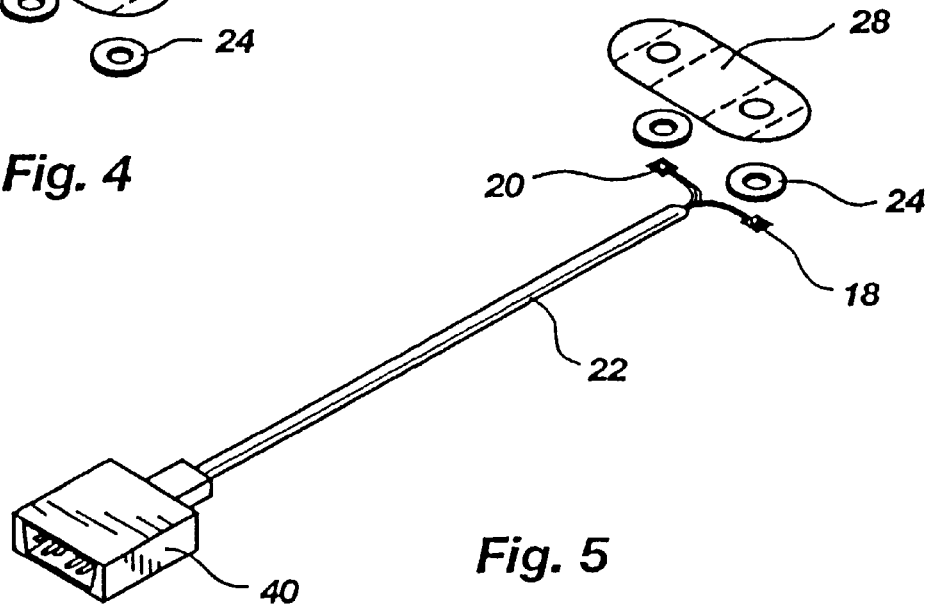
FIG. 5 is a view of the second step of the method of manufacture of the oximetry sensor of the present invention.

Referring to drawing FIG. 5, the cable 22 is provided with a suitable connector 40 on one end thereof while the LED assembly 18 and the photodiode are installed on the appropriate wires of the cable 22 on the other end thereto. The LED assembly 18 and the photodiode 20 are placed within the support rings 24 being retained therein by the adhesive coating on the bottom of the window film 26 while a portion of the cable 22 also engages a portion of the adhesive coating on the window film 26.

Figure 6:
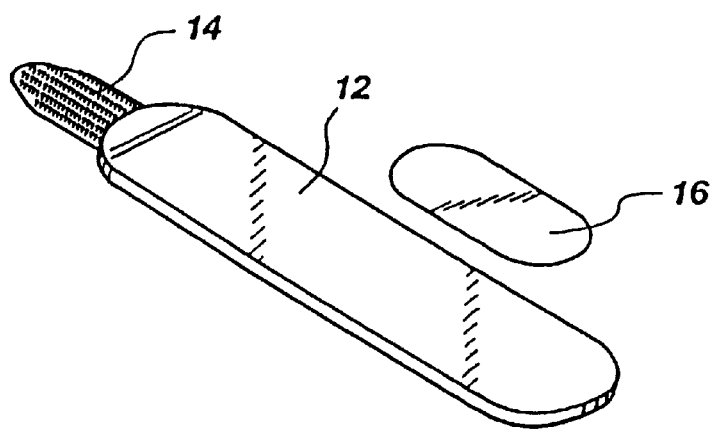
FIG. 6 is a view of the third step of the method of manufacture of the oximetry sensor of the present invention.

Referring to drawing FIG. 6, the foam wrap member 12 has back film mounting member 16 installed thereon by the member 16 adhesively engaging the foam portion 30 of the member 12 as the back film mounting member 16 is formed having an adhesive coating on each side thereof.

Figure 7:
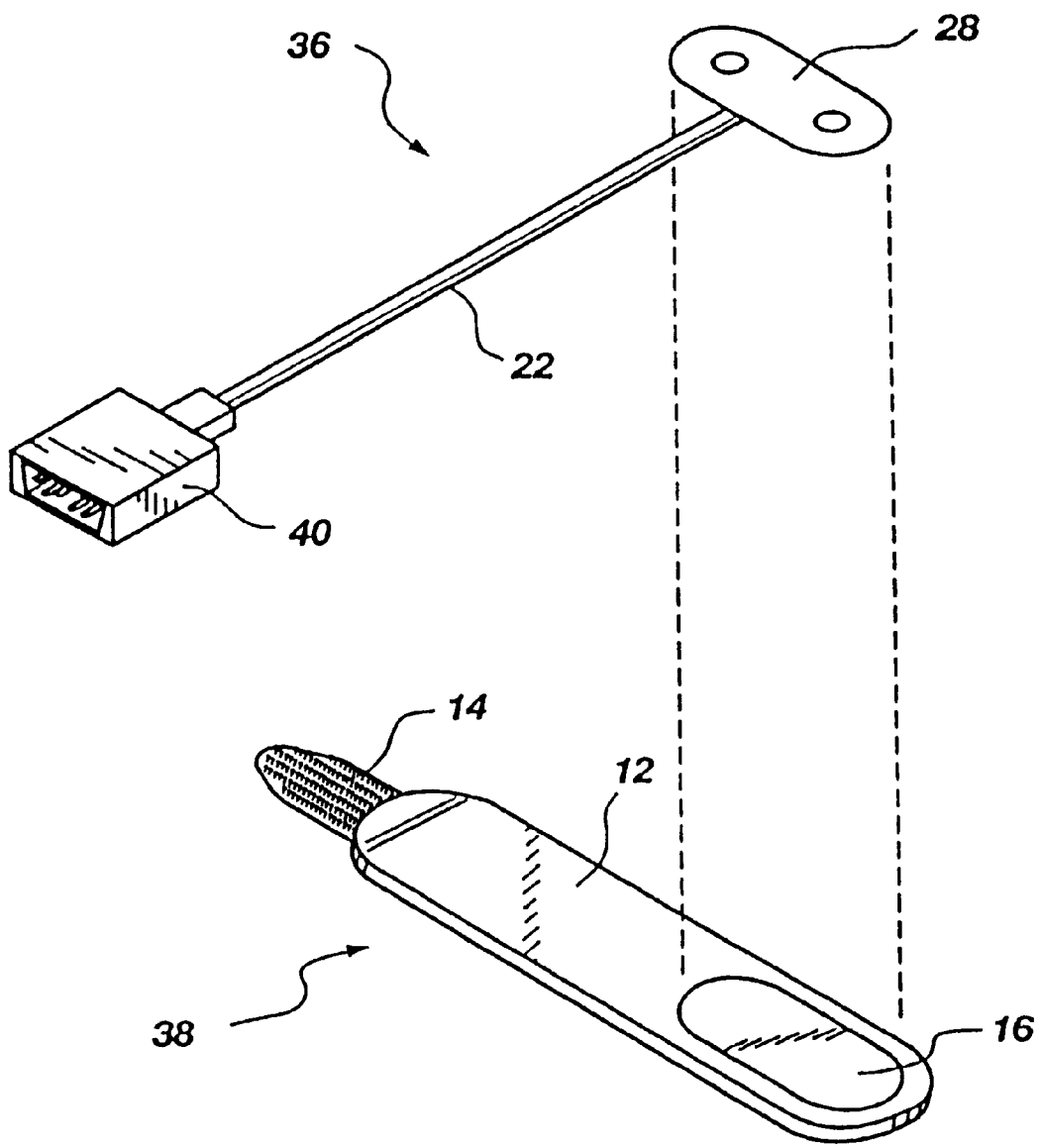
FIG. 7 is a view of the fourth step of the method of manufacture of the oximetry sensor of the present invention.

Referring to drawing FIG. 7, the completed subassembly 36 is shown of the cable 22 having connector 40 on one end thereof and LED assembly 18 and photodiode 20 on the other end thereof while a portion of the cable 22, support rings 24, LED assembly 18, and photodiode 20 are retained by the adhesive coating on the bottom of window film 26 which, in turn, is retained by the adhesive coating on the top of the window film 26 to top liner 28. The completed subassembly 38 is shown of the foam wrap member 12 having back film mounting member 16 adhesively retained thereon. The subassembly 36 is joined to the subassembly 38 by the adhesive coating on the top of back film mounting member 16 engaging the adhesive coating on the bottom of the window film 26. In this manner, the subassembly 36 is securely mounted on the subassembly 38 in the desired position thereon.

Figure 8:
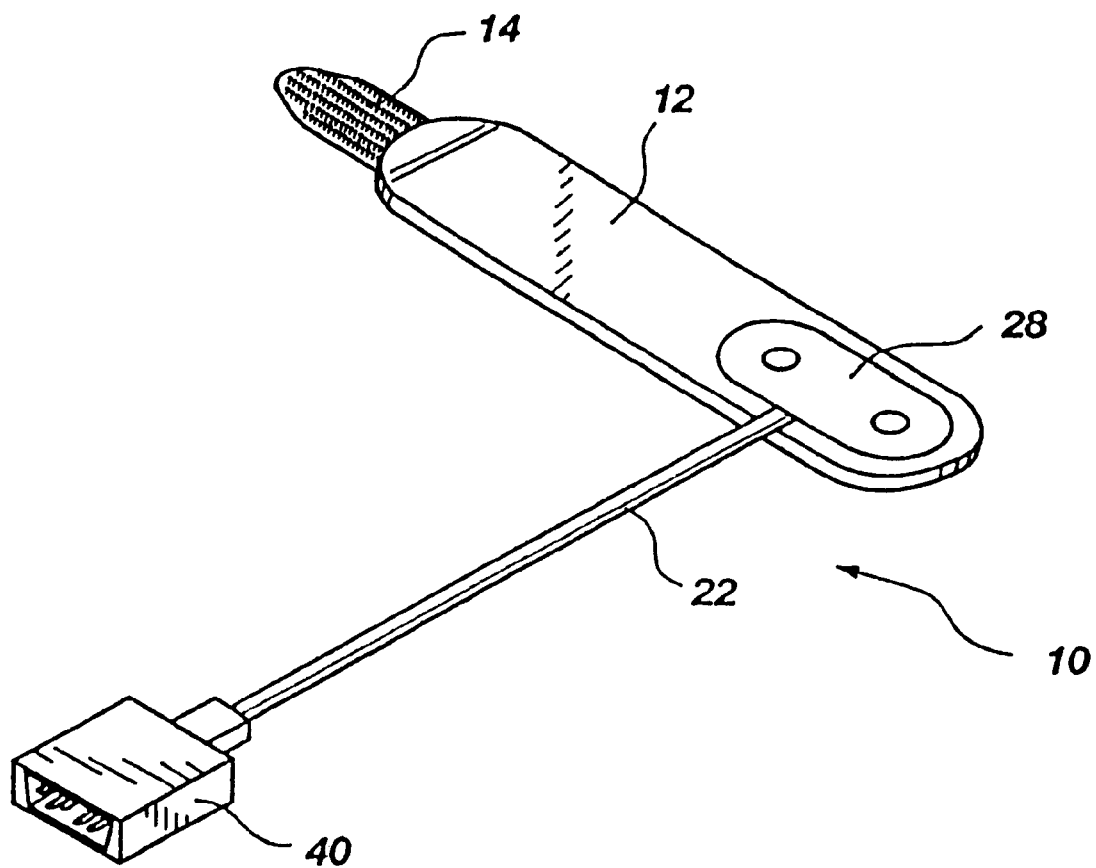
FIG. 8 is a view of the oximetry sensor of the present invention.
Figure 5:
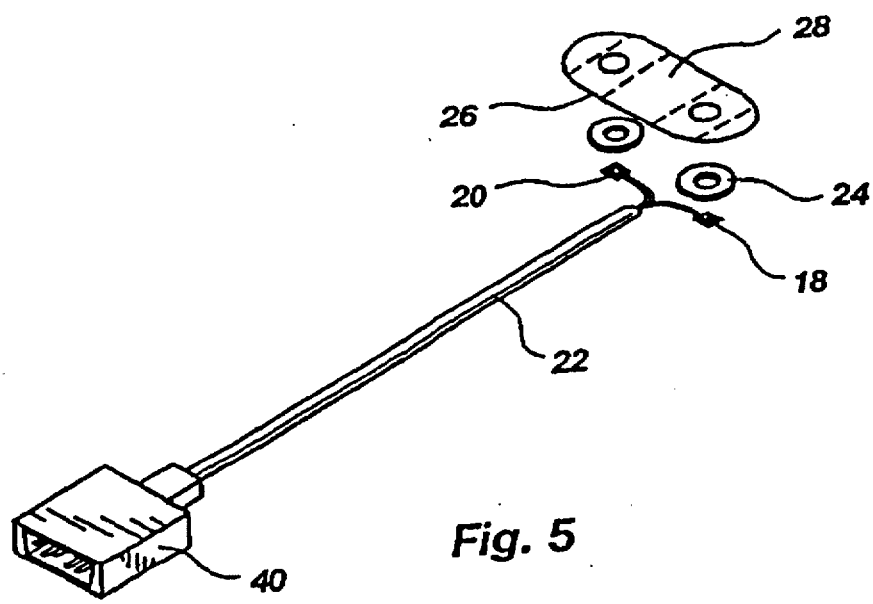
Figure 6:
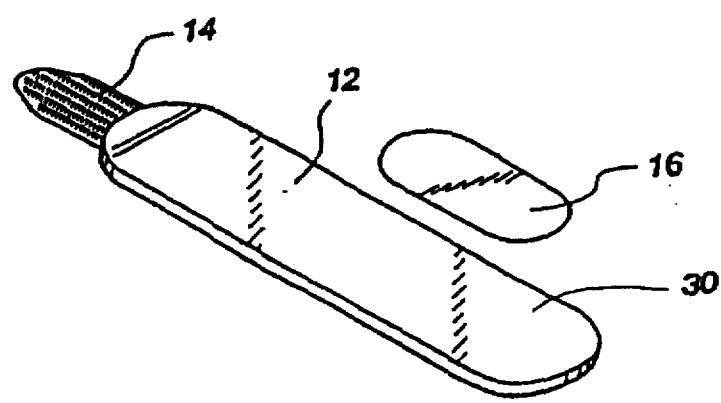
Figure 7:
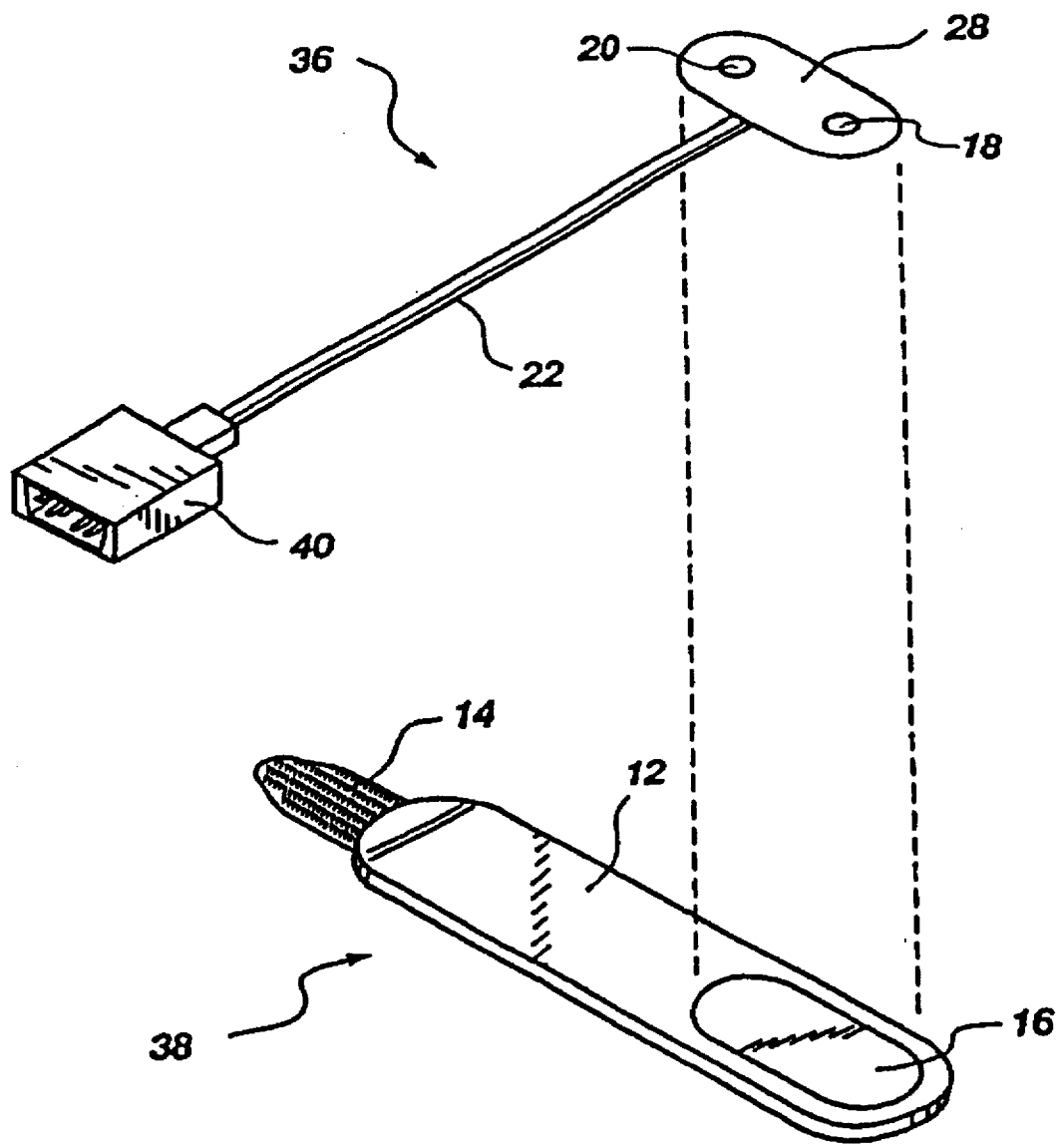

Referring to drawing FIG. 8, the oximetry sensor 10 of the present invention is shown in its assembled, completed form ready for use on a patient.

From the foregoing it is easily seen that the oximetry sensor 10 of the present invention offers any advantages over the prior art sensors. The oximetry sensor 10 is generally easily manufactured from inexpensive materials, is easy to use on a patient, is easy to repeatedly reuse on a patient, and is comfortable in use on a patient. Since the oximetry sensor 10 of the present invention does not use adhesive to attach the sensor 10 to a patient, the sensor 10 is quickly applied to a patient and has no adhesive contacting the skin of a patient to cause discomfort. The oximetry sensor 10 of the present invention is easily adjustable and has an extended life in comparison to adhesively retained sensors. The oximetry sensor 10 also is easy to reposition on a patient for optimum signal and comfort. Additionally, since the foam wrap member is conformable and compressible, the oximetry sensor may be easily repositioned on a patient without unwrapping the sensor from the patient. The combination of the foam wrap and fabric back provides comfort to the patient and a readily conformable sensor. The foam wrap, fabric back, and polyurethane liner also allows the sensor to breath and help minimize sweating of a patient. As such, the oximetry sensor 10 of the present invention is very suitable for use on patients with burns with minimum trauma to the burns. Since the oximetry sensor 10 of the present invention is not retained on the patient through the use of adhesives, the sensor is very suited to patients who may be sensitive or have allergies to adhesives. As previously stated, the sensor 10 is non-traumatic during use since it is conformable and compressible. Since the oximetry sensor 10 is simple to manufacture from relatively inexpensive materials, it is disposable but has a long life during use as compared to adhesive type sensors as well as being readily reusable on a patient. The oximetry sensor 10 of the present invention may be readily trimmed to customize the application of the sensor to a patient. Additionally, the oximetry sensor 10 may be sterilized, if so desired, since the materials from which the sensor is made will accept sterilization.

It can be seen from the foregoing that changes, deletions and modifications to the oximetry sensor of the present invention may be made which fall within the scope of the invention. Additionally, it can be further seen from the foregoing that changes, additions, deletions and modifications to the method of manufacturing the oximetry sensor of the present invention may be made which fall within the scope of the invention.

We claim:

1. An oximetry sensor comprising:
   an elongated foam wrap member including a fastener on one end thereof, the foam wrap member having a foam member having a first side, a second side, and a thickness, the foam member having a fabric member attached thereto on the first side of the foam member;
   an LED assembly and a photodiode located on the second side of the foam member;
   a window film attached to the other end of the second side of the foam member of the foam wrap member for covering the LED assembly and photodiode; and
   a top liner attached to a portion of the window film and covering a portion of the window film.

2. The oximetry sensor of claim 1, further comprising:
   a back film mounting member.

3. The oximetry sensor of claim 1, further comprising:
   support rings for the LED assembly and the photodiode.

4. The oximetry sensor of claim 1, further comprising:
   a cable connected to the LED assembly and the photodiode.

5. The oximetry sensor of claim 2, wherein the back film mounting member is
   adhesively secured to a portion of the foam wrap member.

6. The oximetry sensor of claim 5, wherein the fastener of the foam wrap member includes a plurality of hooks thereon to engage the fabric member of the foam wrap member.

7. The oximetry sensor of claim 6, wherein the fabric member of the foam wrap member includes a plurality of loops therein to engage the plurality of hooks located on the fastener.

8. The oximetry sensor of claim 3, wherein the support rings are adhesively secured to a portion of the window film.

9. The oximetry sensor of claim 1, wherein the support rings are adhesively secured to a portion of the back film mounting member and the window film.

10. The oximetry sensor of claim 1, wherein the top liner is adhesively secured to a portion of the window film.

11. The oximetry sensor of claim 1, wherein the LED assembly and the photodiode are connected to a cable having a connector on one end thereof.

12. The oximetry sensor of claim 11, wherein the cable includes a connector on one end thereof.

13. The oximetry sensor of claim 1, wherein the support rings are adhesively secured to a portion of the back film mounting member and a portion of the window film.

14. An oximetry sensor comprising:
- an elongated foam wrap member including a fastener secured thereto having a plurality of hooks thereon, the foam wrap member having a foam portion secured to a fabric portion, the fastener attached to one end of the elongated foam wrap member;
- a back film mounting member attached to a portion of the foam wrap member adjacent the other end thereof, the back film mounting member attached to a side of the foam portion of the foam wrap member opposite the fabric portion of the foam wrap member;
- an LED assembly and a photodiode, the LED assembly and the photodiode attached to a portion of the back film mounting member;
- a window film covering the LED assembly and the photodiode, the window film secured to a portion of the back film mounting member; and
- a top liner attached to a portion of the back film mounting member, the window film covered by the top liner.

15. The oximetry sensor of claim 14, wherein the back film mounting member is adhesively secured to a portion of the foam wrap member.

16. The oximetry sensor of claim 14, wherein the fastener of the foam wrap member includes a plurality of hooks thereon to engage the fabric portion of the foam wrap member.

17. The oximetry sensor of claim 16, wherein the fabric portion of the foam wrap member includes a plurality of loops therein to engage the plurality of hooks located on the fastener.

18. The oximetry sensor of claim 14, wherein support rings are adhesively secured to a portion of the window film.

19. The oximetry sensor of claim 14, wherein support rings are adhesively secured to a portion of the back film mounting member and the window film.

20. The oximetry sensor of claim 14, wherein the top liner is adhesively secured to a portion of the window film.

21. The oximetry sensor of claim 14, wherein the window film is transparent to red and infrared light.

22. An oximetry sensor comprising:
- an elongated foam wrap member including a fastener having a plurality of hooks thereon, the foam wrap member having a foam portion having a first side and a second side, and having fabric members attached to the first side and the second side of the foam portion, and having the fastener attached to one end of the elongated foam wrap member;
- an LED assembly and a photodiode located on the elongated foam wrap member; and
- a top liner secured to a portion of the foam wrap member adjacent the other end thereof, the top liner securing the LED assembly and the photodiode in position on the foam wrap member.

23. An oximetry sensor comprising:
- an elongated foam wrap member including a fastener having a plurality of hooks thereon, the foam wrap member having a foam portion enclosed by a fabric member, the fastener attached to one end of the elongated foam wrap member;
- an LED assembly and a photodiode located on the elongated foam wrap member; and
- a top liner secured to a portion of the foam wrap member adjacent the other end thereof, the top liner securing the LED assembly and the photodiode in position on the foam wrap member.

* * * * *

UNITED STATES PATENT AND TRADEMARK OFFICE
CERTIFICATE OF CORRECTION

PATENT NO. : 6,073,038
DATED : June 6, 2000
INVENTOR(S) : Wang et al.

Page 1 of 5

It is certified that error appears in the above-identified patent and that said Letters Patent is hereby corrected as shown below:

Drawings,
Fig. 5, insert reference numeral -- 26 -- and indicator line therefor;
Fig. 6, insert reference numeral -- 30 -- and indicator line therefor; and
Fig. 7, insert reference numerals -- 18 -- and -- 20 -- and indicator lines therefor. (See attached new drawings)

Column 1,
Line 4, change "CROSS REFERENCE" to -- CROSS-REFERENCE --;
Line 24, change "light emitting" to -- light-emitting --;
Line 26, change "infra-red" to -- infrared --;
Line 28, change "be then" to -- then be --;
Line 30, change "light emitting" to -- light-emitting --;
Line 32, change "photo diode," to -- photodiode, --;
Line 38, after "art" delete "type" (second occurrence);
Line 43, change "long term" to -- long-term --;
Line 64, after "lower" insert -- the --;

Column 3,
Line 33, after "the" insert -- LED --;
Line 36, change "light emitting" to -- light-emitting --;
Line 37, change "light emitting" to -- light-emitting --;
Line 43, change "infra-red" to -- infrared --;
Line 62, change "rubber like" to -- rubber-like --;

Column 4,
Line 5, change "infra-red" to -- infrared --;
Line 6, after "and" insert -- readily -- and insert -- . -- after "therethrough";
Line 7, delete "readily";
Line 14, change "infra-red" to -- infrared --;
Line 16, delete "coating";
Line 43, change "infra-red" to -- infrared --;
Line 48, before "member" insert -- foam wrap --;
Line 49, before "member" insert -- foam wrap --;
Line 51, before "member" insert -- foam wrap --;
Line 55, before "member" insert -- foam wrap --;
Line 63, before "sensor" insert -- oximetry --;

UNITED STATES PATENT AND TRADEMARK OFFICE
CERTIFICATE OF CORRECTION

PATENT NO.   : 6,073,038
DATED        : June 6,
INVENTOR(S)  : Wang et al.

It is certified that error appears in the above-identified patent and that said Letters Patent is hereby corrected as shown below:

Column 5,
Line 12, after "photodiode" insert -- 20 --;
Line 21, after "of the" insert -- foam wrap --;
Line 44, change "any" to -- many --;
Line 50, after "the" (both occurrences) insert -- oximetry --;
Line 65, change "bums" to -- burns --;
Line 66, change "bums" to -- burns --; and Column 6,
Line 3, after "the" insert -- oximetry --.

Column 6, claim 1,
Line 31, change "the other" to -- another --;
Line 33, after "and" insert -- the --;
Line 35, change "a" to -- another --;

Column 6, clam 3,
Line 38, change "claim 1," to -- claim 2, --;

Column 6, claim 5,
Line 44, delete "hard return" so that text continues on line 44 after "is" with "adhesively secured...";

Column 6, claim 8,
Line 54, change "a portion" to -- another portion --;

Column 6, claim 9,
Line 55, change "claim 1," to -- claim 3, --;

Column 6, claim 10,
Line 59, change "a portion" to -- said portion --;

Column 6, claim 12,
Line 64, change "a" to -- said --;

Column 6, claim 13,
Line 65, change "claim 1," to -- claim 3, --;

UNITED STATES PATENT AND TRADEMARK OFFICE
CERTIFICATE OF CORRECTION

PATENT NO.   : 6,073,038
DATED        : June 6,
INVENTOR(S)  : Wang et al.

It is certified that error appears in the above-identified patent and that said Letters Patent is hereby corrected as shown below:

Column 7, claim 14,
Line 8, change "the other end" to -- to another end --;
Line 16, change "a portion" to -- another portion --;
Line 18, change "a portion" to -- a third portion --;

Column 7, claim 15,
Line 21, change "a portion" to -- said portion --;

Column 7, claim 16,
Line 24, change "a plurality" to -- said plurality --;

Column 7, claim 19,
Line 34, change "a portion" to -- said portion --;

Column 8, claim 22,
Line 16, change "the other" to -- another --; and

Column 8, claim 23,
Line 28, change "the other" to -- another --.

Signed and Sealed this

Sixteenth Day of April, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.    : 6,073,038
DATED         : June 6, 2000
INVENTOR(S)   : Wang et al.

It is certified that error appears in the above-identified patent and that said Letters Patent is hereby corrected as shown below:

Title page,
Item [73], Assignee, change "Technologies" to -- Technology --.

Signed and Sealed this

Twenty-fifth Day of February, 2003

JAMES E. ROGAN
*Director of the United States Patent and Trademark Office*